United States Patent [19]
Wakabayashi et al.

[11] 3,963,766
[45] June 15, 1976

[54] PROCESS FOR SEPARATION OF 19-NOR-Δ⁴-ANDROSTENE-3,17-DIONE

[75] Inventors: Ken-ichi Wakabayashi; Susumu Kanno, both of Machida, Japan

[73] Assignee: Mitsubishi Chemical Industries Ltd., Tokyo, Japan

[22] Filed: Jan. 31, 1975

[21] Appl. No.: 545,900

[30] Foreign Application Priority Data
Feb. 26, 1974 Japan............................. 49-22534

[52] U.S. Cl............................ 260/397.3; 260/239.5
[51] Int. Cl.²..................... C07J 1/00; C07J 43/00
[58] Field of Search...................... 260/397.3, 239.5

*Primary Examiner*—Elbert L. Roberts
*Attorney, Agent, or Firm*—Oblon, Fisher, Spivak, McClelland & Maier

[57] ABSTRACT

In a process for separating 19-nor-Δ⁴-androstene-3,17-dione from a mixture of steroids which is obtained by the Birch reduction of an alkyl or an aralkyl ether of estrone acetal having the following formula (I),

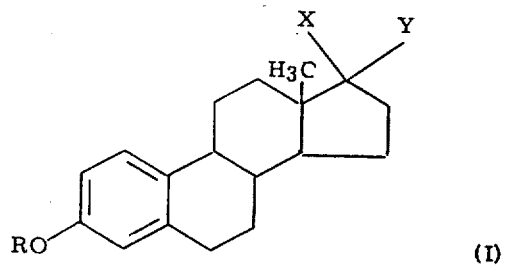

(I)

wherein R is selected from the group consisting of an alkyl group containing 1 to 10 carbon atoms and an aralkyl group containing a side chain of 1 to 5 carbon atoms; X and Y are selected from the group consisting of O-alkyl and S-alkyl groups, respectively, containing 1 to 10 carbon atoms; or the following formula (II), $$\begin{pmatrix} (CH_2)_n \\ Z \qquad W \end{pmatrix}$$

(II)

wherein R is as defined above; Z and W are selected from the group consisting of oxygen atom and sulfur atom; and n represents an integer of from 2 to 10; followed by the hydrolysis of the obtained reduction product of said Birch reduction, the improvement which comprises 1. reacting said mixture of steroids containing 19-nor-Δ⁴-androstene-3,17-dione with a secondary amine to form the $C_3$-enamine of 19-nor-Δ⁴-androstene-3,17-dione,
2. extracting the resultant $C_3$-enamine of 19-nor-Δ⁴-androstene-3,17-dione with an aqueous solution of an inorganic acid, and then
3. hydrolyzing the separated $C_3$-enamine of 19-nor-Δ⁴-androstene-3,17-dione.

15 Claims, No Drawings

PROCESS FOR SEPARATION OF 19-NOR-Δ⁴-ANDROSTENE-3,17-DIONE

BACKGROUND OF THE INVENTION

1. Field of the Invention

The present invention relates to a process for separation of 19-nor-Δ⁴-androstene-3,17-dione. More particularly, the present invention relates to a process for effectively separating 19-nor-Δ⁴-androstene-3,17-dione (hereinafter abbreviated as ESD) in high purity as the $C_3$-enamine from a mixture of steroids.

2. Description of Prior Art

ESD, whose structure is illustrated by formula (A) below, is important as a preparative intermediate for a corpus luteum hormone, 19-nor-ethisterone, whose structure is shown by the following formula (B). The latter is obtained by ethynylation of ESD, and is useful as a main component of oral contraceptive pills. ESD is obtained by hydrolysis of the $C_3$-enamine of ESD.

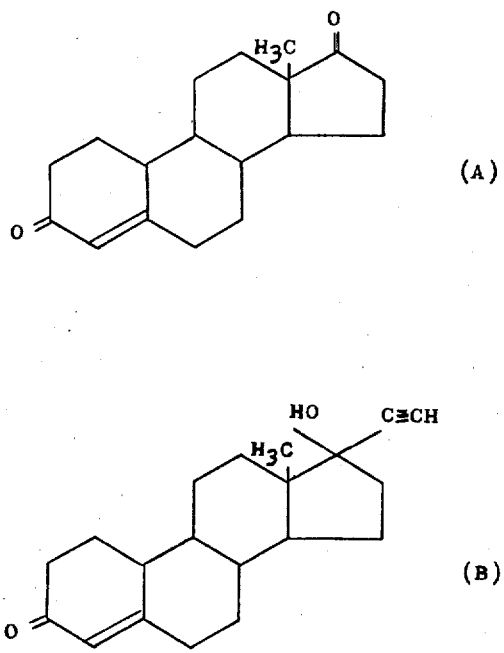

The principal technique for production of ESD is by Birch's reduction of an alkyl or aralkyl ether of estrone acetal, shown below by formulas (I) and (II), respectively, followed by hydrolysis of the product. However, in the past, it has been difficult to control the conversion of Birch's reduction, and the number of species and the quantities of by-products formed in the reaction have been found to vary widely depending upon the nature of the conversion. That is, in the above reaction, double-bond isomers such as 19-nor-Δ¹-androstene-3,17-dione, 19-nor-Δ¹,⁽¹⁰⁾-androstene-3,17-dione, 19-nor-Δ⁵-androstene-3,17-dione and the like; or 19-nor-androstane-3,17-dione and the like, in which the carbon-carbon double bond is completely hydrogenated, are formed as by-products in the formation of ESD. Additionally, the alkyl or aralkyl ether of estrone is formed by acetal hydrolysis from the alkyl or aralkyl ether of estrone acetal.

When the conversion percentage of Birch's reduction is high, a slight drop in the selectivity of the formation of ESD occurs. When the degree of conversion, defined as 100%- the percentage of unreacted starting material, becomes higher than 98%, especially higher than 99.5%, the amount of the 19-nor-androstane-3,17-dione produced in the saturated form increases rapidly. In view of this, it is preferred that the conversion of Birch's reduction be maintained below 99.5%, more preferably below 98%. On the other hand, it is found that if the conversion of Birch's reduction is lowered as described above, the alkyl or aralkyl ether of estrone formed by hydrolysis of the starting material is produced along with ESD. In addition, the alkyl or aralkyl ether of estrone becomes ethynylated, producing a compound showing strong estrogenic hormone action. Therefore, it is necessary to remove the alkyl or aralkyl ether of estrone from ESD prior to said ethynylation reaction. Furthermore, from an economical viewpoint, this by-product must be recovered for reuse.

Attempts have been made to separate the desired ESD from the mixture of steroids. One such technique attempted is by column chromatography. However, it has been found that separation of ESD by such a process is almost impossible on an industrial scale since ESD and the above described by-products are very similar in their physical properties.

Another method attempted for separating ESD from a mixture containing the steroids obtained by Birch's reduction and hydrolysis is by recrystallization. However, pure ESD cannot be obtained by this process either. This is because the alkyl or aralkyl ether of estrone, which is always present in the mixture of steroids as a result of low conversion of Birch's reduction, required to avoid the formation of undesired saturated 19-nor-androstane-3,17-dione, as previously described, crystallizes far more readily than either the desired ESD or the other by-products. Consequently, the crystals of ESD invariably become contaminated by the alkyl or aralkyl ether of estrone.

Still another attempted process for obtaining ESD is based on the known process for separating Δ⁴-3-ketosteroids from ketones, or nonketonic materials, which are soluble in organic solvents and inert to the enamine formation reaction. This process comprises forming the enamines from a mixture of steroids containing Δ⁴-3-ketosteroids, converting the obtained enamine derivatives of Δ⁴-3-ketosteroids to their hydrochlorides, hydrobromides or hydroiodides by respectively adding hydrogen chloride, hydrogen bromide of hydrogen iodide, and then taking advantage of the solubilities of the said hydrochlorides in organic solvents such as methanol and the like or the insolubilities of the same in organic solvents, such as benzene-ether (1:1) or the like, or the insolubilities of the hydrobromides or hydroiodides in organic solvents, such as methanol or the like. (See J. Am. Chem. Soc. 78 434 (1956)). However, the ESD counterpart of the above process is troublesome and cannot be applied on an industrial scale. The reason is that in Birch's reduction of an alkyl or an aralkyl ether of estrone acetal followed by hydrolysis the control of conversion is relatively difficult and the species and the quantities of by-products are liable to fluctuate as mentioned previously. Since the conditions for selectively separating enamine salts of Δ⁴-3-ketosteroids vary to a large extend depending upon the number of species and the relative quantities of the steroids present, the separation procedure would necessarily have to be varied continuously depending upon the conversion percentage of Birch's reduction. Furthermore, the alkyl or aralkyl ether of estrone which is formed by hydrolysis of the alkyl or aralkyl ether of estrone acetal in the course of Birch's reduction and subsequent hydrolysis is only soluble in organic solvents with difficulty, while the other products of said reaction are readily soluble in organic solvents.

Therefore, in separating the hydrochloride of $C_3$-enamine of ESD by taking advantage of the insolubility of said hydrochloride in organic solvents, such as benzene-ether (1:1) or the like, the enamine salt is contaminated by an alkyl or an aralkyl ether of estrone. This can be avoided if the HCl is introduced after the difficultly soluble alkyl or aralkyl ether of estrone, is first completely dissolved. However, as shown in Comparative Example 1, when it is attempted to completely dissolve the alkyl or an aralkyl ether of estrone so as to avoid contamination, 1 g of the reaction product of Birch's reduction and hydrolysis containing about 13% of the alkyl ether of estrone (87% conversion of Birch's reduction) cannot be dissolved in 100 ml of benzene-ether (1:1). Hence, the separation process is not appropriate for industrial use, since a large excess of said solvent must be used to obtain the enamine salt in high purity.

Consequently, it would be desirable to have a process for separating pure ESD from the Birch's reduction and hydrolysis reaction mixture by a process suitable for industrial use.

SUMMARY OF THE INVENTION

Accordingly, one object of the present invention is to provide an industrially suitable process for effectively separating ESD, which is useful as a preparative intermediate for corpus luteum hormone as previously described, in high purity from a mixture of steroids.

More specifically, it is an object of the present invention to provide a process for separating the main product, ESD, which is obtained by effectuating Birch's reduction of an alkyl or an aralkyl ether of estrone acetal in less than 99.5%, more preferably less than 98.5% conversion, followed by hydrolysis, from by-products, such as the alkyl or the aralkyl ether of estrone, 19-nor-androstane-3,17-dione and double bond isomers, such as 19-nor-$\Delta^1$-androstene-3,17-dione or the like.

These and other objects of this invention, as will hereinafter be made clear by the discussion below, have been attained by 1. reacting a mixture of steroids which is obtained by the Birch's reduction of an alkyl or an aralkyl ether of estrone acetal having the following formula (I).

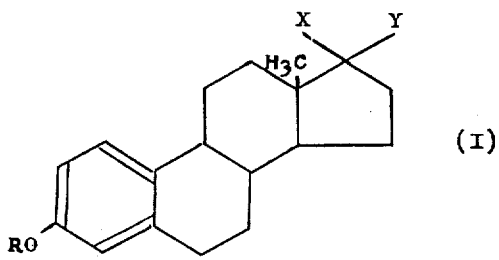

(I)

wherein R is selected from the group consisting of an alkyl group containing 1 to 10 carbon atoms and an aralkyl group containing a side chain of 1 to 5 carbon atoms; X and Y are selected from the group consisting of O-alkyl and S-alkyl groups, respectively, containing 1 to 10 carbon atoms; or the following formula (II),

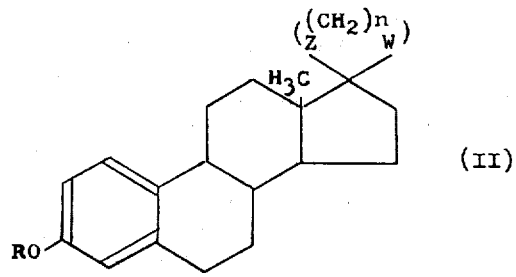

(II)

wherein R is selected from the group consisting of an alkyl group containing 1 to 10 carbon atoms and an aralkyl group containing a side chain of 1 to 5 carbon atoms; Z and W are selected from the group consisting of oxygen atom and sulfur atom; and n represents an integer of from 2 to 10;

followed by the hydrolysis of the obtained reaction product of said Birch's reduction with a secondary amine to form the $C_3$-enamine of ESD, 2. extracting the so-formed $C_3$-enamine of ESD with an aqueous solution of an inorganic acid, and then
3. hydrolyzing the separated $C_3$-enamine of ESD.

When the above method is employed, the following characteristics are observed:

1. The $C_3$-enamine of 19-nor-$\Delta^1$-androstene-3,17-dione is obtained with high selectivity.
2. Said enamine derivative is fairly stable in an aqueous solution of an inorganic acid and can be selectively separated with high efficiency by using the usual operation of extraction with an aqueous solution of an inorganic acid having an appropriate pH.
3. The contaminating alkyl ether of estrone can be separated with high efficiency and can be reused as a starting material for the reactions after conversion to the corresponding acetal.
4. ESD can be obtained in high purity by alkali hydrolysis of the enamine derivative after it has been extracted with an aqueous solution of an inorganic acid.

DESCRIPTION OF PREFERRED EMBODIMENTS

Suitable alkyl or aralkyl ethers of estrone acetal for use as the starting material for the present invention are shown by the above formulas (I) and (II). R in these formulas includes a lower alkyl group containing generally 1–10 carbon atoms, preferably 1–5 carbon atoms such as a methyl group, an ethyl group, an n-propyl group, an n-butyl group, an n-hexyl group, or the like, or an aralkyl group containing a side chain of generally 1–5 carbon atoms, such as a benzyl group, a phenethyl group or the like. X and Y in the above formula (I) include a lower alkoxy group or a lower alkylthio group containing generally 1–10 carbon atoms, preferably 1–5 carbon atoms, such as methoxy group, an ethoxy group, an n-butoxy group, a methylthio group, an ethylthio group, an n-butylthio group or the like. Cyclic acetals at the 17 position in the above formula (II) include an alkylenedioxy group or an alkylenedithio group containing generally 2–10 carbon atoms, preferably 2–5 carbon atoms, such as an ethylenedioxy group, a trimethylenedioxy group, an ethylenedithio group, a trimethylenedithio group and the like.

The Birch's reduction and the hydrolysis of the ethers of estrone acetals, are carried out in the usual manner. It is known that the $C_3$-enamine can be obtained in a subsequent enamine formation reaction of steroids. As has been previously described, in Birch's reduction and hydrolysis of an alkyl or an aralkyl ether of estrone acetal, many steroids which have carbonyl groups at the 3- and 17-positions are obtained. The enamines of these other products are also extracted with an aqueous solution of an inorganic acid unless precautions are taken to insure that the $C_3$-enamine of ESD is selectively obtained. Therefore, it is necessary to select appropriate conditions for the enamine formation reaction to satisfactorily attain the ultimate object of separation. For example, according to the most general process for enamine formation, wherein steroids arae refluxed in benzene in the presence of a secondary amine using p-toluenesulfonic acid as catalyst, both the $C_3$-enamine and $C_{17}$-enamine are obtained. Also, according ot the process wherein steroids are refluxed in benzene in the presence of a secondary amine without a catalyst, the $C_3$enamine is not selectively obtained. However, it has now been determined that the $C_3$-enamine of ESD can be formed with high selectivity by using alcohol series solvents. Suitable alcohol series solvents include the aliphatic alcohols, such as methanol, ethanol, propanol, isopropanol, n-butanol or the like, phenols, such as phenol, cresol or the like; aralkyl alcohols, such as benzyl alcohol, phenethyl alcohol or the like; and cycloaliphatic alcohols, such as cyclohexanol, cyclopentanol or the like. The preferred alcohol series solvents are methanol and ethanol. In addition, the above solvents may be used as mixtures of two or more solvents, or as mixtures of the above solvents with other solvents not alcohols.

The enamine formation reaction is carried out by reacting a mixture of steroids with a suitable secondary amine, such as pyrrolidine, piperidine, morpholine, dimethylamine or the like preferably pyrrolidine, at a temperature in the range of 0°C to room temperature for a period of from 5 minutes to 5 hours. Upon completion of the enamine formation reaction, an organic solvent which is readily separable from water is added. Alternatively, the alcohol series solvent used as the solvent for the reaction is distilled off. Then, the ESD formed is extracted with an aqueous solution of an inorganic acid. It is preferred that after evaporation of the alcohol series solvent an organic solvent which is readily separable from water is then added to dissolve or suspend the reaction product of said enamine formation reaction. Then the $C_3$-enamine of ESD is extracted from the resulting solution or suspension with an aqueous solution of an inorganic acid. It is also preferred that the newly added solvent readily dissolve the reaction products of Birch's reduction followed by hydrolysis. These include alkyl ethers of estrone or the like. Furthermore, the solvent should be readily separable from water, stable in inorganic acids, and readily recoverable. Suitable solvents preferred for use include benzene, toluene, chloroform, methylene chloride, dichloroethane, trichloroethane, diethyl ether, ethyl acetate or the like.

ESD can also be separated from a mixture of steroids in a process wherein upon evaporation of the alcohol series solvent, the reaction mixture resulting from the enamine formation reaction is stirred together with an aqueous solution of a mineral acid. The insoluble mixture of steroids is then filtered off and the soluble $C_3$-enamine of ESD is separated. A third process suitable for separation of the $C_3$-enamine consists of the following steps: upon completion of the enamine formation reaction, the enamine which is insoluble in the alcohol series solvent is filtered off; the separated enamine is dissolved in a solvent, preferably, such as benzene, chloroform and the like; and the $C_3$-enamine of ESD is extractively separated with an aqueous solution of an inorganic acid.

Furthermore, the ESD finally formed can be obtained in higher purity by separating the small amount of by-product steroids contained in the aqueous solution of the inorganic acid used for the extractive separation of the $C_3$-enamine of ESD. This can be accomplished by extracting the aqueous solution of the inorganic acid with the newly added solvent e.g., benzene, etc.

The aqueous solution of the inorganic acid to be used for the extractive separation of said enamine should have a pH preferably below a pH of 3, more preferably below a pH of 1. If the pH value is higher than the above and approaches the neutral point, the enamine derivative will be distributed with a higher content in the organic layer rather than in the water layer. Consequently, it becomes difficult to separate the enamine derivative as an enamine salt. Suitable inorganic acids include hydrochloric acid, sulfuric acid, nitric acid, hydrogen bromide, hydrogen iodide, phosphoric acid, sodium hydrogen sulfate, sodium hydrogen sulfite and the like. The quantity of acid used should be more than one equivalent per one equivalent of the amine used for the enamine formation reaction, and more preferably more than 1.5 equivalents. It is known that the enamine derivative is hydrolyzed quickly when heated in alcohol or allowed to stand in an aqueous solution of an organic acid such as acetic acid, p-toluenesulfonic acid and the like. However, it is stable to the above-specified highly concentrated aqueous solutions of inorganic acids, such as, especially, hydrochloric acid, sulfuric acid, hydrogen bromide and the like.

Finally, ESD can be obtained by hydrolyzing the $C_3$-enamine of ESD selectively separated with the aqueous solution of the inorganic acid as above described. For example, most of the enamine derivative is hydrolyzed by neutralizing the aqueous solution of the inorganic acid of the enamine derivative with an alkali metal, an alkaline earth metal or a hydroxide thereof. Preferred neutralizing agents include sodium hydroxide, potassium hydroxide, lithium hydroxide, and calcium hydroxide; or a salt of a weak acid such as carbonate and the like, for example, sodium carbonate, potassium carbonate and the like. When the solution is allowed to stand neutral or in some cases under alkaline conditions with or without stirring for a period of one to two hours, or when said solution is heated with or without stirring, ESD is obtained in quantitative yield as a result of hydrolysis of the $C_3$-enamine. The temperature of neutralization is not critical and can be arbitrarily selected. Generally, preferred temperatures are in the vicinity of room temperature. The time required for neutralization is also not critical. Generally, sufficient yields are obtained within 1 hour.

The above hydrolysis yields the secondary amine used in the enamine formation reaction together with ESD. However, since ESD is used as a pharmaceutical intermediate, this contamination of ESD with a secondary amine should be avoided. For this purpose, the following additional processing can be employed: the alkaline hydrolysis solution is made acidic and then ESD is separated; or preferably, ESD is extracted with an organic solvent which is readily separable from water and which readily dissolves ESD, such as benzene, chloroform and ethyl acetate, and then the amine is removed by washing said organic solvent containing the extracted ESD with an acid aqueous solution. As has been described in detail above, according to the present invention, the desired ESD is obtained in high purity and selectivity with good reproducibility employing a simple operation. The process can be used even though the conversion and selectivity of Birch's reduction fluctuate to a large extent. Moreover, the present invention makes it possible to treat the desired enamine derivative of ESD in an aqueous solution during the entire period from its separation to its recovery without ever removing it. Consequently, the operation is very easy and advantageous from the industrial viewpoint and minimizes the loss of the desired product. This process for separation of ESD is thus both economical and superior in yield and quality of product to the processes of the past.

Having generally described the invention, a more complete understanding can be obtained by reference to certain specific Examples, which are included for purposes of illustration only and are not intended to be limiting unless otherwise specified.

EXAMPLE 1

To a reaction mixture (conversion 32%, selectivity of ESD 92%, purity 29.4%) which was obtained by Birch's reduction of 5 g of estrone methyl ether ethylene acetal followed by hydrolysis with hydrochloric acid according to the usual procedure, were added 50 ml of methanol and 1.2 ml of pyrrolidine, and the reaction was carried out at room temperature for 2 hours. The resulting reaction mixture was extracted with 150 ml of benzene and 25 ml of 15% hydrochloric acid to separate the water layer. After the water layer was counter-extracted with 5 ml of benzene, the residue was made alkaline with 3N NaOH and and stirred at room temperature for 2 hours. ESD which precipitated during stirring was extracted with benzene. The benzene layer was washed with 1N HCl and water, and dried. Evaporation of benzene yielded 1.11 g of ESD. (Purity was 95% and the separation ratio of 91%. Purity was determined by gas chromatography here and in all the Examples. The separation ratio represents the ratio of separated ESD to ESD formed by Birch's reduction and hydrolysis.)

EXAMPLE 2

To a reaction mixture (conversion 88.1%, selectivity of ESD 90%, purity 79.4%) obtained by Birch's reduction of 5.0 g of estrone ethyl ether, ethylene acetal followed by hydrolysis according to the usual procedure, were added 15 ml of ethanol and 2 ml. of pyrrolidine, and the reaction was carried out for 1.5 hours. Extractive separation was effectuated with 50 ml of chloroform and 40 ml of 4N HCl, and the resultant water layer was made alkaline with 3N NaOH. Using a procedure analogous to that of Example 1, 3.17 g of ESD was obtained. (purity 96%, separation ratio of ESD 94%.)

EXAMPLE 3

To a reaction mixture (conversion 96%, selectivity of ESD 89%, purity 86.4%) obtained by Birch's reduction of 5 g of estrone ethyl ether ethylene acetal followed by hydrolysis according to the usual procedure, were added a mixed solvent consisting of 15 ml of benzene, 15 ml of methanol and 5 ml of phenol, and 1.5 ml of pyrrolidine, and the reaction was carried out at room temperature for 2 hours. 20 ml of the solvent was distilled off under reduced pressure at 40°C. The residue was extracted twice with 50 ml of 2N sulfuric acid and 50 ml of benzene and the separated water layer was made alkaline with 3N NaOH. Using a procedure analogous to that of Example 1, 3.40 g of ESD was obtained. (purity 97%, separation ratio of ESD 96.4%.)

EXAMPLE 4

To a reaction mixture (conversion 94.5%, selectivity of ESD 78%, purity 73.7%) obtained by Birch's reduction of 2 g of estrone methyl ether ethylene acetal followed by hydrolysis according to the usual procedure, were added 20 ml of n-butanol, 2 g of cresol and 1 ml of pyrrolidine, and the reaction was carried out at 40°C for 3 hours. Upon cooling, the extractive separation was effectuated with 50 ml of 10% sodium hydrogen sulfate and 50 ml of ethyl acetate, and the water layer was made alkaline with 5N NaOH. Using a procedure analogous to that of Example 1, 1.15 g of ESD was obtained. (purity 93%, separation ratio of ESD 87.8%.)

EXAMPLE 5

To a reaction mixture (conversion 66.7%, selectivity of ESD 91.2%, purity 60.8%) obtained by Birch's reduction of 5 g of estrone methyl ether ethylene acetal followed by hydrolysis according to the usual procedure, were added 20 ml of ethanol, 20 ml of chloroform, 5 ml of phenol and 1.2 ml of pyrrolidine, and the reaction was carried out at room temperature for 3 hours. The reaction product was extracted with 50 ml of 10% hydrochloric acid and 50 ml of chloroform and the water layer was separated. The water layer was washed with 10 ml of chloroform, separated and made alkaline with 3N potassium carbonate. Using a procedure analogous to that of Example 1, 2.36 g of ESD was obtained. (purity 95%, separation ratio of ESD 89%.)

EXAMPLE 6

To 1 g of a reaction mixture (conversion 87.0%, selectivity 90.4%, purity 78.8%) obtained by Birch's reduction of estrone methyl ether ethylene acetal followed by hydrolysis according to the usual procedure, were added 3 ml of methanol and 0.5 ml of pyrrolidine, and the resulting solution was stirred at room temperature for 2 hours. After addition of 50 ml of benzene, the reaction mixture was extracted with 150 ml of 0.167% hydrochloric acid solution (pH about 1.1, about 1.15 equivalents relative to pyrrolidine), and the water layer was separated. The water layer was neutralized with 3N NaOH, and using a procedure analogous to that of Example 1, 0.567 g of ESD was obtained. (separation ratio of ESD 72%, purity 96%.)

EXAMPLE 7

5 ml of benzene soluton of the enamine of said steroid obtained by the enamine formation reaction of Example 6 was diluted with 50 ml of benzene, and the resulting solution was extracted with 1.5 l of 0.00167% hydrochloric acid solution (pH about 3, 1.15 equivalents relative to pyrrolidine), and the water layer was separated. Using a procedure analogous to that of Example 6, 0.035 g of ESD was obtained. (separation ratio of ESD 41%, purity 93%.)

COMPARATIVE EXAMPLE 1

A mixture of steroids (conversion 87%, selectivity of ESD 90.4%, purity 78.8%) obtained by Birch's reduction followed by hydrolysis with hydrochloric acid according to the usual procedure, was subjected to the enamine formation reaction with pyrrolidine in methanol. Methanol and pyrrolidine were removed in vacuum to obtain a powder. 1 g of the obtained power did not dissolved into 100 ml of dry benzene-ether (1:1) at room temperature (20°C).

COMPARATIVE EXAMPLE 2

A mixture of steroids (conversion 65%, selectivity of ESD 90%, purity 58.5%) obtained by Birch's reduction and hydrolysis was subjected to the enamine formation reaction by the procedure of Comparative Example 1. 1 g of the resulting powder was dissolved into a dry solvent of benzene-ether (1:1) at room temperature (20°C) to form a saturated solution, and HBr gas was introduced. Oily substances adhered to the glass surface, and crystals of the enamine salt of ESD could not be obtained.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. In a process for separating 19-nor-$\Delta^4$-androstene-3,17-dione from a mixture of steroids which is obtained by the Birch reduction of an alkyl or an aralkyl ether of estrone acetal having the following formula (I),

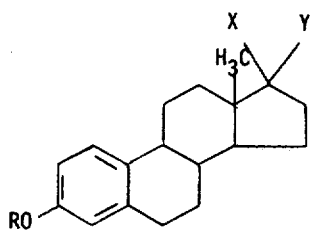

wherein R is selected from the group consisting of an alkyl group containing 1 to 10 carbon atoms and an aralkyl group containing a side chain of 1 to 5 carbon atoms; X and Y are selected from the group consisting of O-alkyl and S-alkyl groups, respectively, containing 1 to 10 carbon atoms; or the following formula (II):

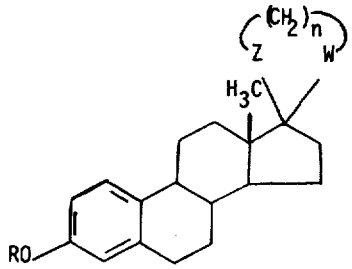

wherein R is as defined above; Z and W are selected from the group consisting of oxygen atom and sulfur atom; and $n$ represents an integer of from 2 to 10; followed by the hydrolysis of the obtained reduction product of said Birch reduction, the improvement which comprises:

1. reacting said mixture of steroids containing 19-nor-$\Delta^4$-androstene-3,17-dione with a secondary amine selected from the group consisting of pyrrolidine piperidine, morpholine and dimethylamine, to form the $C_3$-enamine of 19-nor-$\Delta^4$-androstene-3,17-dione;
2. extracting the resultant $C_3$ enamine of 19-nor-$\Delta^4$-androstene-3,17 dione with an aqueous solution of an inorganinc acid selected from the group consisting of hydrochloric acid, sulfuric acid, nitric acid, hydrobromic acid, hydroiodic acid, phosphoric acid, sodium hydrogen sulfate and sodium hydrogen sulfite, and then;
3. hydrolyzing the separated $C_3$-enamine of 19-nor-$\Delta^4$-androstene-3,17-dione.

2. The process of claim 1, wherein R is selected from the group consisting of methyl, ethyl, n-propyl, n-butyl, n-hexyl, benzyl and phenethyl; X and Y are selected from the group consisting of methoxy, ethoxy, n-butoxy, methylthio, ethylthio and n-butylthio; and —Z—$(CH_2)_n$—W— is selected from the group consisting of ethylenedioxy, trimethylenedioxy, ethylenedithio and trimethylenedithio.

3. The process of claim 1, wherein the alkyl ether of estrone acetal is estrone methyl ether ethylene acetal.

4. The process of claim 1, wherein the alkyl ether of estrone acetal is estrone ethyl ether ethylene acetal.

5. The process of claim 1, wherein the conversion percentage of said Birch's reduction is below 98.5%.

6. The process of claim 1, wherein the enamine formation reaction of said mixture of steroids is carried out in an alcohol solvent.

7. The process of claim 6, wherein said alcohol solvent is selected from the group consisting of methanol and ethanol.

8. The process of claim 1, wherein said secondary amine is pyrrolidine, piperidine, morpholine, or dimethylamine.

9. The process of claim 1, wherein the enamine formation reaction is carried out in an alcohol solvent and the extraction of the formed $C_3$-enamine of 19-nor-$\Delta^4$-androstene-3,17-dione with an aqueous solution of an inorganic acid is effectuated by
  1. evaporating the alcohol solvent,
  2. adding a second solvent of benzene, toluene, chloroform, methylene chloride, dichloroethane, trichloroethane, diethyl ether or ethyl acetate, which is readily separable from water and which readily dissolves the alkyl or aralkyl ether of estrone in order to dissolve or suspend the reaction product of said enamine formation reaction,
  3. extracting said $C_3$-enamine dissolved or suspended in said second solvent with an aqueous solution of an inorganic acid, and then
  4. extracting by-product steroids contained in the aqueous solution of the inorganic acid used for extraction of said $C_3$-enamine with said second solvent.

10. The process of claim 1, wherein the pH of the aqueous solution of the inorganic acid is below 1.

11. The process of claim 1, wherein more than 1.5 equivalents of said inorganic acid per one equivalent of said secondary amine is used.

12. The process of claim 1, wherein the hydrolysis of said $C_3$-enamine is effectuated by adding an alkali into said aqueous solution of the inorganic acid containing said extracted $C_3$-enamine.

13. The process of claim 12, wherein said alkali is selected from the group consisting of sodium hydroxide and potassium hydroxide.

14. The process of claim 1, wherein said secondary amine which is used for the enamine formation reaction and is formed during the hydrolysis of said $C_3$-enamine is removed by washing the solution which is obtained by extraction of the separated 19-nor-$\Delta^4$-androstene-3,17-dione with chloroform, benzene or ethy acetate which is readily separable from water and which readily dissolves 19-nor-$\Delta^4$-androstene-3,17-dione, with an aqueous acid solution.

15. In a process for separating 19-nor-$\Delta^4$-androstene-3,17-dione from a mixture of steroids which is obtained by the Birch's reduction with less than 98.5% conversion, of an alkyl or an aralkyl ether of estrone acetal having the following formula (I),

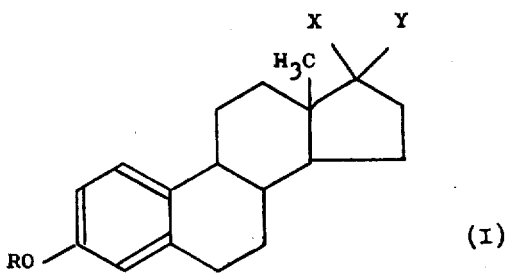

wherein R is selected from the group consisting of an alkyl group containing 1 to 10 carbon atoms and an aralkyl group containing a side chain of 1 to 5 carbon atoms; X and Y are selected from the group consisting of O-alkyl and S-alkyl groups, respectively, containing 1 to 10 carbon atoms; or the following formula (II),

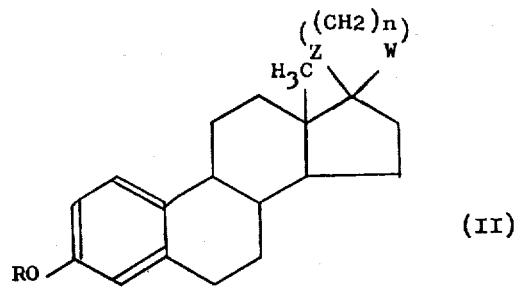

wherein R is as defined above; Z and W are selected from the group consisting of oxygen atom and sulfur atom; and $n$ represents an integer of from 2 to 10; followed by the hydrolysis of the obtained product of said Birch's reduction, the improvement which comprises 1. reacting said mixture of steroids containing 19-nor-$\Delta^4$-androstene-3,17-dione with a secondary amine in an alcohol solvent to form the $C_3$-enamine of 19-nor-$\Delta^4$-androstene-3,17-dione,
2. evaporating the alcohol solvent,
3. adding a second solvent which is readily separable from water and which readily dissolves the alkyl or aralkyl ether of estrone, in order to dissolve or suspend the reaction product of said enamine formation reaction,
4. extracting said $C_3$-enamine dissolved or suspended in said second solvent with an aqueous solution of an inorganic acid, the pH of which is below 1,
5. extracting by-product steroids contained in the aqueous solution of the inorganic acid used for extraction of said $C_3$-enamine, with said second solvent,
6. hydrolyzing the separated $C_3$-enamine of 19-nor-$\Delta^4$-androstene-3,17-dione by adding an alkali into said aqueous solution of the inorganic acid containing said extracted $C_3$-enamine,
7. extracting 19-nor-$\Delta^4$-androstene-3,17-dione which is obtained by said hydrolysis of the $C_3$-enamine of 19-nor-$\Delta^4$-androstene-3,17-dione, with an organic solvent which is readily separable from water and which readily dissolves 19-nor-$\Delta^4$-androstene-3,17-dione, and then,
8. removing said secondary amine which is used for the enamine formation reaction and which is formed during the hydrolysis of said $C_3$-enamine by washing the solution which is obtained by extraction of the separated 19-nor-$\Delta^4$-androstene-3,17-dione with said organic solvent, with an aqueous acid solution.

* * * * *